United States Patent [19]

Iwamura et al.

[11] Patent Number: 4,472,432
[45] Date of Patent: Sep. 18, 1984

[54] MEDICINAL USE OF α,β-UNSATURATED FATTY ACIDS

[75] Inventors: Junichi Iwamura, Kashiwara; Chozo Hayashi, Nishinomiya; Nozomu Takeuchi, Ibaragi, all of Japan

[73] Assignee: Inabata & Co., Ltd., Osaka, Japan

[21] Appl. No.: 377,407

[22] Filed: May 12, 1982

[51] Int. Cl.$^3$ .............................................. A61K 31/20
[52] U.S. Cl. ..................................................... 424/318
[58] Field of Search ......................................... 424/318

[56] References Cited

U.S. PATENT DOCUMENTS

| | | | |
|---|---|---|---|
| 3,982,017 | 9/1976 | Thiele | 424/318 |
| 4,097,604 | 6/1968 | Thiele | 424/318 |
| 4,215,144 | 7/1980 | Thiele | 424/318 |

FOREIGN PATENT DOCUMENTS 2349090  4/1975  Fed. Rep. of Germany ...... 424/318

*Primary Examiner*—Frederick E. Waddell
*Attorney, Agent, or Firm*—Hubbell, Cohen, Stiefel & Gross

[57] ABSTRACT

A medicinal composition which comprises a compound of the formula:

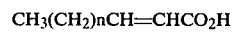

wherein n represents 10, 12, 14 or 16, or a pharmaceutically acceptable salt thereof and a pharmaceutically acceptable carrier; a method for testing diabetes or improving lipid metabolism by the administration of said composition to a human being; and a process for the separation of said compounds from freshwater clam which comprises subjecting freshwater clam to the extraction with hot water and/or an aprotic solvent and then purifying the resultant.

9 Claims, No Drawings

MEDICINAL USE OF α,β-UNSATURATED FATTY ACIDS

BACKGROUND OF THE INVENTION

1. Field of the Invention:

This invention relates to a medicinal use of α,β-unsaturated fatty acids, more particularly to a medicinal composition containing α,β-unsaturated higher fatty acids, and to a method for treating diabetes or improving lipid metabolism by the administration of said composition to a human being, and to a process for separating said compounds from freshwater clam by extraction.

2. Description of the Prior Art:

Freshwater clams such as *Corbicula sandai* belonging to Corbiculidae have long been believed to be effective for treating liver disease, and various studies have been made on the pharmaceutical effectiveness of freshwater clams.

For example, thoracic duct lymph-accelerating effect, liver function-enhancing effect, bile acid secretion-increasing effect, etc. of a freshwater clam extract have been reported. Further, effective ingredients contained in freshwater clams showing the above-described pharmacological effects have been studied as well, and some reports say that amino acids such as methionine, cystine, cystinic acid, etc. are responsible for liver function-enhancing effect.

However, ingredients obtained by extraction of freshwater clams have not been studied with a view toward improving lipid metabolism. This may be attributed to the consideration that shellfish including clams are usually rich in choresterol, Also, such ingredients have not been studied as possible therapeutic agents for diabetes.

Under such circumstances, the inventors of the present invention have examined the pharmacological effects of substances which are obtained by extracting the whole part of freshwater clams with hot water, concentrating the water extract and extracting it with an aprotic solvent, and which are obtained by drying the fleshy part isolated after said extraction with hot water and then extracting the dried fleshy part with an aprotic solvent. It has been found that said substances possess the effect of improving lipid metabolism (prophylaxis and remedy of hyperlipemia, lipotropic effect, and propylaxis of arteriosclerosis), and the effect for curing diabetes. As a result of further investigations, the inventors have isolated specific four specific α,β-unsaturated higher fatty acids from the above-described substance and have concluded that they are the ingredients responsible for the above-described pharmacological effects, thus having achieved the present invention.

SUMMARY OF THE INVENTION

This invention provides a medicinal composition comprising a compound or a mixture of compounds represented by the following formula:

$$CH_3(CH_2)_nCH=CHCO_2H$$

(wherein n represents 10, 12, 14 or 16) or a pharmaceutically acceptable salt thereof and a pharmaceutically acceptable carrier, and a method for treating diabetes or improving lipid metabolism by administering a therapeutically effective dosage of the composition to a human being.

In addition, the present invention provides a process for preparing the compounds of the above-described formula, which comprises subjecting the whole part of a freshwater clam or its fleshy portion as such or as finely cut pieces to either one of steps (i) or (ii):

(i) hot-extraction with water at about neutrality, concentration of the aqueous extract, then extraction of the concentrate and/or the separated fleshy portions with an aprotic solvent; and (ii) extraction with an aprotic solvent, and removing the solvent from the resulting extract and then purifying through column chromatography or the like.

DESCRIPTION OF THE PREFERRED EMBODIMENTS

The pharmacologically effective ingredients to be used in the present invention are α,β-unsaturated higher fatty acids represented by the following formula:

$$CH_3(CH_2)_nCH=CHCO_2H$$

(wherein n represents 10, 12, 14 or 16) or pharmaceutically acceptable salts thereof specifically, 2-tetradecenoic acid, 2-hexadecenoic acid, 2-octadecenoic acid, and 2-eicosenoic acid and pharmaceutically acceptable salts thereof. The pharmaceutically acceptable salts include alkali metal salts such as the sodium or potassium salts.

These α,β-unsaturated fatty acids have been found to possess the effect of curing diabetes and the effect of improving lipid metabolism.

The present invention provides a medicinal composition comprising the above-described α,β-unsaturated fatty acid or a pharmaceutically acceptable salt thereof and a pharmaceutically acceptable carrier, which can be used for prophylaxis and remedy of hyperlipemia, arteriosclerosis, liver troubles such as fatty liver and hepatitis, and for prophylaxis and remedy of diabetes.

Further, the present invention provides a method for treating diabetes or improving lipid metabolism which comprises administering to a human being a therapeutically effective dosage of a composition comprising a compound of the following formula:

$$CH_3(CH_2)_nCH=CHCO_2H$$

(wherein n represents 10, 12, 14 or 16) or a pharmaceutically acceptable salt thereof and a pharmaceutically acceptable carrier.

The dosage of the effective ingredients of the present invention varies depending upon the degree of disease, weight of a human to be treated therewith, etc. but, in the case of oral administration to adults, they are administered 2 to 3 times a day, with each administration being conducted generally in a dosage of 50 to 500 mg, preferably 100 to 300 mg.

As the preparation form for administering the effective ingredients, there are tablets, capsules (including ordinary capsules retaining granular medicines and soft capsules retaining a liquid sealed therein), and liquids for oral administration.

Also, they may be used in the form of, for example, injections or drops to be introduced into the body.

The compounds of the present invention are so susceptible to solvolysis or oxidation that they, in any preparation form, are preferably kept out of contact with ambient atmosphere. Water and alcohol are not generally suitable solvents because they accelerate hydrolysis of the effective ingredients. Thus, as a liquid carrier, anhydrous and oily substances such as oleic acid, linoleic acid, linolenic acid, etc. are preferably used.

As a specific example of preferable preparation form, there are capsules (soft capsules) wherein a liquid mixture of the above-described linoleic acid and the pharmaceutically effective ingredients is sealed. Tablets are also a preferably preparation form. In forming tablets, the pharmaceutically effective ingredients of the present invention, alone or a mixture of the ingredients, and linoleic acid are adsorbed on a suitable solid carrier and compressed into tablets. If necessary, the tablets may be coated with a suitable coating agent.

As the above-described solid carrier, there are illustrated, for example, lactose, starch, carboxymethyl cellulose, dextrin, calcium phosphate, calcium carbonate, synthetic or natural calcium silicate, magnesium oxide, dry aluminum hydroxide, magnesium stearate, sodium bicarbonate, dry yeast, etc.

In addition, an antioxidant may be compounded in the preparation. Further, those disintegrators, corrigents, sweetenings, colorants, etc. which are used in this field may properly be added unless they accelerate hydrolysis or oxidation of the effective ingredients of the present invention.

In a different aspect of the present invention, a process is provided for separating the aforesaid $\alpha,\beta$-unsaturated fatty acids from freshwater clams by extraction.

Freshwater clams to be used in the present invention include *Corbicula sandai, Corbicula leana, Corbicula japonica* and similar species, which belong to Corbiculidae. Of those, the use of *Corbicula sandai* Reinhardt is preferable.

According to the process of the present invention, the whole body or fleshy portions of freshwater clams are used as such or in finely cut pieces, and:
 (i) they are hot-extracted with water at about neutrality, the aqueous extract is concentrated, then the concentrate and/or the separated fleshy portions are extracted with an aprotic solvent; or
 (ii) they are extracted with an aprotic solvent, and the solvent is removed from the extract and the residue purified to separate $\alpha,\beta$-unsaturated fatty acids.

With route (i), water to be used for hot-extraction with water is preferably in a boiled state. The freshwater clam is preferably extracted without separating fleshy portions from shells. Upon extraction, water is used in an amount 2 to 10 times by weight, preferably 4 to 5 times, as much as that of Corbicula. This extraction treatment is conducted for 3 hours to 10 hours, preferably 4 to 5 hours. After hot-extraction treatment with water, the aqueous extract is concentrated, and the resulting concentrate and the previously extracted fleshy portions are then extracted with an aprotic solvent.

As the aprotic solvent to be used in this extraction procedure, there are used hydrocarbons such as straight- or branched-chain, saturated hydrocarbons, alicyclic hydrocarbons, aromatic hydrocarbons, etc.; halogenated hydrocarbons such as dichloromethane, chloroform, carbon tetrachloride, etc.; dimethylsulfoxide; dimethylformamide; acetonitrile; ketones such as acetone and methyl ethyl ketone; diethyl ether; etc. Of these, saturated chain hydrocarbons are preferable, with n-hexane being most preferable.

In extraction procedure, the concentrate of the above-described aqueous extract is preferably in a powdery state, and the extracted fleshy portions are preferably dried and cut into pieces as small as possible.

Upon extraction procedure, these substances to be extracted are preferably well dispersed in a solvent to realize high contact efficiency with the solvent. For example, the extraction in an ultrasonic wave bath is preferable.

With route (ii), the same aprotic solvent as with route (i) are used. Upon extraction procedure, the substances to be extracted are preferably dried and cut into fine pieces.

The substance obtained by removing the solvent from the above-described aprotic solvent extract is a mixture containing increased amounts of the aforesaid $\alpha,\beta$-unsaturated fatty acids. The mixture has a diabetescuring effect and a lipid metabolism-improving effect in the as-produced crude form.

The above-described crude product is further purified. For such purification, column chromatography is useful.

As a column support to be filled in a column to be used in column chromatography, silica gel is preferable and, as the eluting solvent, hexane, benzene, ethyl ether, methanol, or benzene-methanol mixture is suitably used.

According to a preferred purifying method, the concentrate obtained by concentrating the above-described aprotic solvent extract is placed on the column and eluted with successive, hexane, benzene, ethyl ether, and methanol. The end products of the present invention are eluted with benzene and ethyl ether in a purified form.

For isolation of pure products of the compounds of the present invention, it is desirable to further conduct chromatography using successively, hexane, benzene, ethyl ether, and methanol as eluting solvents.

The end compounds of the present invention are finally eluted in the ethyl ether fraction described above.

Additionally, all of the materials obtained in the step of further purifying the above-described aprotic solvent extract show the effect of curing diabetes and the effect of improving lipid metabolism.

The present invention will now be described in more detail by reference to pharmacological experiments and Examples.

PHARMACOLOGICAL EXPERIMENT 1

(Effect on ethanol-induced fatty liver)

(1) Animals used:
Male Sprague Dawley rats weighing 200 g.
(2) Testing method:
Two groups of the respective 6 rats described above were used: one group being control group (A); and the other being fatty liver-induced group (B) to which 2 ml/100-g body weight of a 50% ethanol aqueous solution had been aministered for consecutive ten days by one administration in the morning through a gastric tube. Further, to group (C) of 5 rats described above were intraperitoneally administered 0.5 ml/100-g body weight of a solution prepared by dissolving 200 mg of 2-octadecenoic acid in 5 ml of olive oil (corresponding to 10 mg of 2-octadecenoic acid per 100-g body weight)

simultaneously with administration of a 50% ethanol aqueous solution in the same manner as with group (B).

After completion of the above-described administration, rats were decapitated, and blood was collected to measure the amounts of total cholesterol (Chol), triglyceride (TG), phospholipid (PL) of blood serum, and the amounts of total lipid, Chol, TG, and PL in liver. Results thus obtained are tabulated in Tables 1 and 2.

TABLE 1

| Tested Animal Group | Results of measurement of blood serum lipids | | |
|---|---|---|---|
| | Chol (mg/100 ml) | TG (mg/100 ml) | PL (mg/100 ml) |
| Control Group (A) | 5.04 ± 3.21 | 91.2 ± 10.14 | 88.6 ± 8.40 |
| Ethanol-administered Group (B) | 74.3 ± 5.58$^a$ | 141.8 ± 10.06$^a$ | 94.7 ± 13.98 |
| Ethanol and 2-Octadecenoic Acid-administered Group (C) | 59.8 ± 2.18 | 125.8 ± 2.85 | 137.0 ± 21.54 |

Note
$^a$Significant difference was observed over control group (A).

TABLE 2

| Tested Animal Group | Results of measurement of liver lipids | | | |
|---|---|---|---|---|
| | Total Lipid Amount (mg/100 ml) | Chol (mg/100 ml) | TG (mg/100 ml) | PL (mg/100 ml) |
| Control Group (A) | 36.2 ± 1.34 | 1.93 ± 0.13 | 4.08 ± 0.63 | 22.67 ± 1.19 |
| Ethanol-administered Group (B) | 50.1 ± 3.43$^a$ | 3.21 ± 0.24$^a$ | 9.51 ± 0.78$^a$ | 23.07 ± 0.82 |
| Ethanol and 2-Octadecenoic Acid-administered Group (C) | 38.6 ± 1.52$^b$ | 2.44 ± 0.11$^b$ | 6.86 ± 0.99 | 24.15 ± 0.30 |

Notes
$^a$Significant over control group (A).
$^b$Significant over ethanol-administered group (B).

From the above results, it follows that, in comparison with control group (A), ethanol-administered group (B) underwent an increase in total cholesterol amount and triglyceride amount in blood serum and total lipid amount, total cholesterol amount, and triglyceride amount in liver with significant difference, but underwent only a slight increase in phospholipid amount in blood serum and liver without significant difference.

Comparison of ethanol-administered group (B) with ethanol- and 2-octadecenoic acid-administered group (C) is as follows. With group (C), total cholesterol amount and triglyceride amount of blood serum increased in group (B) with significant difference by adminstration of ethanol were observed to tend to be decreased. On the other hand, total lipid amount and cholesterol amount in liver, which were increased by administration of ethanol with signicicant difference, were decreased with significant difference, with triglyceride amount of blood serum and liver being in a decreasing tendency. As is described above, 2-octadecenoic acid can be said to possess the effect of decreasing the total cholesterol amount and triglyceride amount of blood serum and total lipid amount, total cholesterol amount, and triglyceride amount of liver which were increased by ethanol-induced fatty liver.

Further, histological examination of tested rats revealed that fat droplets observed with alcohol-administered group rats by dyeing with Sudan III were remarkably decreased with group (C) rats.

PHARMACOLOGICAL EXPERIMENT 2

(Effect on orotic acid-induced fatty liver)

(1) Animals used:
Male Sprague Dawley rats weighing 200 g.
(2) Testing method:
Three groups of the respective 8 rats described above were used. One group received ordinary powdery diet (control group (A)). Another group received the same powdery diet as given to group (A) except for adding thereto 1.5 g/kg of orotic acid-administered group (B)). The other group received the same powdery diet as given to group (A) except for adding thereto 1.5 g/kg of orotic acid and 1.0 g/kg of 2-octadecenoic acid a day (orotic acid- and 2-octadecenoic acid-administered group (C)). The above-described administration was conducted for consecutive ten days with all groups, followed by autopsy to measure liver weight and total lipid amount, Chol, TG, and PL of liver. Results thus obtained are tabulated in Table 3.

TABLE 3

| Tested Animal Group | Liver Weight (g/100 g) | Total Lipids of Liver (mg/100 g) | Chol (mg/100 g) | TG (mg/100 g) | PL (mg/100 g) |
|---|---|---|---|---|---|
| Control Group (A) | 3.61 ± 0.077 | 180 ± 12.3 | 9.14 ± 0.177 | 5.34 ± 0.843 | 102 ± 3.70 |
| Orotic Acid-administered Group (B) | 4.57 ± 0.322$^a$ | 444 ± 33.4$^a$ | 17.71 ± 0.898$^a$ | 74.48 ± 11.7$^a$ | 143 ± 4.63$^a$ |
| Orotic Acid- and 2-Octadecenoic Acid-administered Group (C) | 4.01 ± 0.130$^b$ | 305 ± 39.5$^b$ | 13.34 ± 0.941$^b$ | 39.8 ± 10.16$^b$ | 120 ± 5.10$^b$ |

Notes
$^a$significant over control group (A)
$^b$significant over orotic acid-administered group (B)

From the above results, it is seen that, in comparison with control group (A), orotic acid-administered group (B) underwent a significant increase in liver weight and total lipid amount, Chol, TG, and PL of liver and that, in comparison with orotic acid-administered group (B), orotic acid- and 2-octadecenoic acid-administered group (C) underwent a signicifant decrease in every analysis item. Thus, it is clear that 2-octadecenoic acid is effective against orotic acid-induced fatty liver.

PHARMACOLOGICAL EXPERIMENT 3

(Effect on D-galactosamine-induced liver trouble)

(1) Animals used:
Male Wistar rats weighing 200 g.

(2) Testing method:
Three groups of the respective 6 rats described above were used. One group was control group (A). Another group was fasted for 18 hours, then intraperitoneally administered with 450 mg/kg of D-galactosamine and, after 22 hours, autopsied (group (B)). The other group were administered with 1.0 g/kg of 2-octadecenoic acid (using a preparation obtained by dissolving 2-octadecenoic acid in ether, mixing the solution with a 2-fold quantity of lactose, drying and suspending in a 0.5% methyl cellulose aqueous solution) two hours before the same administration of D-galactosamine as with group (B) and, 22 hours after administration of D-galactosamine, autopsied (group (C)). Enzyme activity of glutamic pyruvic transaminase (GPT) and glutamic oxaloacetic transaminase (GOT) of the blood serum obtained by autopsy, liver weight, and total lipid amount in liver were measured to obtain the results given in Table 4.

TABLE 4

| Tested Animal Group | Serum GPT | Serum GOT | Liver Weight (g/100 g) | Total Lipids of Liver (g/100 g) |
|---|---|---|---|---|
| Control Group (A) | 29 ± 5 | 208 ± 19 | 3.42 ± 0.07 | 4.49 ± 0.10 |
| D-Galactosamine-administered Group (B) | 302 ± 87[a] | 643 ± 142[a] | 4.04 ± 0.07[a] | 5.04 ± 0.21[a] |
| D-Galactosamine- and 2-Octadecenoic Acid-administered Group (C) | 27 ± 3[b] | 214 ± 24[b] | 3.66 ± 0.07[b] | 4.95 ± 0.24[b] |

Notes
[a]significant over control group (A)
[b]significant over D-galactosamine-administered group (B)

The above results reveal that, in comparison with control group (A), D-galactosamine-administered group (B) underwent an increase in every measurement item with significant difference. In comparison with this group (B), D-galactosamine- and 2-octadecenoic acid-administered group (C) underwent a decrease in GPT and GOT in blood serum and liver weight with significant difference, with total lipid amount in liver being in a decreasing tendency. From these, it follows that 2-octadecenoic acid has an effect against D-galactosamine-induced liver trouble.

Additionally, when two groups of the respective 10 male and female Wistar rats (200 g) were orally administered with 5 g/kg and 10 g/kg, respectively, of 2-octadecenoic acid (dissolved in olive oil) for consecutive 5 days, there were observed no abnormality.

PHARMACOLOGICAL EXPERIMENT 4

(Effect on streptozotocin-induced diabetes)

(1) Animals used:
Male Sprague-Dawley rats weighing 200 g.

(2) Testing method:
Two groups of the respective 6 rats described above were used. One group was control group (A), and the other group was injected with 50 mg/kg of streptozotocin through tail vein to cause diabetes (confirmed by urinous sugar examination)(group B). Of group (B) rats, three rats were orally loaded, after 20 days, with 1.0 g/kg of 2-octadecenoic acid together with diet. After 10 days, Chol, TG, PL, and free fatty acid (FFA) of blood serum, blood sugar in hunger (FBS), and total lipid amount, Chol, TG, and PL of liver were examined with every group to obtain the results shown in Tables 5 and 6.

(3) Results of experiments:
Table 5 shows that, in comparison with control group (A), streptozotocin-administered group (B) underwent a slight increase in TG and FFA, and a significant increase in Chol, PL and FBS. 2-Octadecenoic acid-administered group (C) underwent a significant increase in Chol in comparison with group (A), and underwent a significant increase in FBS in comparison with group (B).

Table 6 shows that, in comparison with control group (A), streptozotocin-administered group (B) underwent an increase in total lipid amount, a decrease in Chol, and a significant increase in TG and PL. On the other hand, Chol, 2-octadecenoic acid-administered group (C) was lower than that of group (A) or (B), and TG was lower than that of group (B). Total lipid amount and PL of group (C) were significantly lower than those of group (B). From these, it follows that 2-octadecenoic acid has the effect of improving or curing liver function or the effect of decreasing blood sugar against diabetes.

TABLE 5

| Tested Animal Group | Chol (mg/dl) | TG (mg/dl) | PL (mg/dl) | FFA (mEg/l) | FBS (mg/dl) |
|---|---|---|---|---|---|
| Control Group (A) | 61.2 ± 2.06 | 172.3 ± 17.12 | 104.0 ± 3.33 | 0.75 ± 0.066 | 121.5 ± 5.06 |
| Streptozotocin-Group (B) | 78.9 ± 3.94[a] | 190.4 ± 20.29 | 136.4 ± 13.54[a] | 0.83 ± 0.059 | 464.4 ± 41.41[a] |
| Streptozotocin and 2-Octadecenoic acid-administered | 74.3 ± 6.35[a] | 147.4 ± 15.20 | 94.1 ± 15.48 | 0.74 ± 0.098 | 190.9 ± 67.51[b] |

TABLE 5-continued

| Tested Animal Group | Chol (mg/dl) | TG (mg/dl) | PL (mg/dl) | FFA (mEg/l) | FBS (mg/dl) |
| --- | --- | --- | --- | --- | --- |
| Group (C) | | | | | |

Notes:
[a]significant over control group (A)
[b]significant over streptozotocin-administered group (B)

TABLE 6

| Tested Animal Group | Total Lipid in Liver (mg/g) | Chol (mg/g) | TG (mg/g) | PL (mg/g) |
| --- | --- | --- | --- | --- |
| Control Group (A) | 42.43 ± 2.849 | 2.64 ± 0.301 | 5.08 ± 1.033 | 21.86 ± 0.480 |
| Streptozotocin-adminstered Group (B) | 48.12 ± 2.836 | 2.57 ± 0.145 | 7.61 ± 0.901[a] | 28.04 ± 0.688[a] |
| Streptozotocin and 2-Octadecenoic acid-administered Group (C) | 37.32 ± 2.768[b] | 2.23 ± 0.097 | 5.53 ± 1.036 | 23.76 ± 1.452[b] |

Notes:
[a]significant over control group (A)
[b]significant over streptozotocin-administered group (B)

EXAMPLE 1

800 Kg of Corbicula were boiled in water, and an aqueous solution was spray-dried to obtain 6.4 kg of aqueous extract powder, with fleshy portions being separated from shells and dried by hot air to obtain 11.7 kg of a dried product.

These were extracted with n-hexane in a supersonic wave bath to obtain 1.4 kg of a viscous, blackish-brown oil.

This oil was subjected to column chromatography (using 700 g of 60 to 80-mesh silica gel filled in a glass tube of 5 cm in diameter and 100 cm in length). As eluting solvents, 1 liter each of hexane, benzene, ethyl ether, and methanol were used in this order. A latter 200 ml portion of benzene fraction and a former 200 ml portion of ethyl ether fraction were collected. They were concentrated to obtain 700 g of an oil, which was subjected to the same column chromatography as described above, followed by concentrating a benzene fraction and an ethyl ether fraction in the same manner as described above to obtain 400 g of an oil. This oil was further subjected to column chromatography using hexane, benzene, ethyl ether, and methanol in this order as eluting solvents. Thus, 21.5 g of an oil containing compounds forming color by irradiation with UV light (observed on TLC) was obtained from the former portion of the ethyl ether fraction.

This oil was methylated with diazomethane in a conventional manner, and the resulting methyl esters were analyzed by gas chromatography to obtain a gas chromatogram constituted by four main peaks. Compounds corresponding to respective peaks were gas-chromatographically collected and analyzed through infrared absorption, NMR, amd mass spectrum and, as a result, the thus obtained data were found to completely coincide with the spectral data of separately synthesized methyl 2-tetradecenoate, methyl 2-hexadecenoate, methyl 2-octadecenoate, and methyl 2-eicosenoate.

Additionally, these acids were solids at room temperature (26° C.), and are comparatively stable compounds though being modified by solvolysis or oxidation.

What is claimed is:

1. A method for treating diabetes or improving lipid metabolism which comprises administering orally or parenterally to a human being a therapeutically effective dosage of a composition comprising a compound of the formula:

$CH_3(CH_2)_nCH=CHCO_2H$ wherein n represents 10, 12, 14 or 16, or a pharmaceutically acceptable salt thereof and a pharmaceutically acceptable carrier.

2. The method of claim 1 wherein said therapeutically effective dosage comprises about 50–500mg of said compound.

3. The method of claim 1 wherein said therapeutically effective dosage comprises about 100–300mg of said compound.

4. The method of claim 1 wherein said composition is administered 2 to 3 times a day.

5. The method of claim 1 wherein said compound is selected from the group consisting of 2-tetratdecenoic acid, 2-hexadecenoic acid, 2-octadecenoic acid, and 2-eicosenoic acid.

6. The method of claim 1 wherein said pharmaceutically acceptable salt is an alkalai metal salt.

7. The method of claim 1 wherein said pharmaceutically acceptable salt is selected from the group consisting of sodium and potassium salts.

8. The method of claim 1 wherein said pharmaceutically acceptable carrier is a liquid carrier selected from the group consisting of oleic acid, linoleic acid, linolenic acid, and olive oil.

9. The method of claim 1 wherein said pharmaceutically acceptable carrier is a solid carrier selected from the group consisting of lactose, starch, carboxymethylcellulose, dextrin, calcium phosphate, calcium carbonate, synthetic or natural calcium silicate, magnesium oxide, dry aluminum hydroxide, magnesium stearate, sodium bicarbonate, and dry yeast.

* * * * *